US008982532B2

(12) United States Patent
Iyer

(10) Patent No.: US 8,982,532 B2
(45) Date of Patent: Mar. 17, 2015

(54) FILTERED FEEDTHROUGH ASSEMBLY AND ASSOCIATED METHOD

(71) Applicant: Medtronic, Inc., Minneapolis, MN (US)

(72) Inventor: Rajesh V. Iyer, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/765,539

(22) Filed: Feb. 12, 2013

(65) Prior Publication Data
US 2013/0215553 A1 Aug. 22, 2013

Related U.S. Application Data

(63) Continuation of application No. 12/368,847, filed on Feb. 10, 2009, now Pat. No. 8,373,965.

(51) Int. Cl.
H01G 4/35 (2006.01)
A61N 1/375 (2006.01)
H01G 4/236 (2006.01)

(52) U.S. Cl.
CPC .............. *H01G 4/35* (2013.01); *A61N 1/3754* (2013.01); *H01G 4/236* (2013.01)
USPC ........ 361/302; 361/305; 361/307; 361/301.1; 361/298.2; 361/304

(58) Field of Classification Search
USPC ........... 361/301.1, 298.2, 302, 305, 307, 304, 361/600
See application file for complete search history.

(56) References Cited

U.S. PATENT DOCUMENTS

| 3,464,405 A | 2/1972 | Wallis |
| 3,803,875 A | 4/1974 | Root |
| 3,920,888 A | 11/1975 | Barr |
| 4,152,540 A | 5/1979 | Duncan |
| 4,285,730 A | 8/1981 | Sanford |
| 4,314,031 A | 2/1982 | Sanford |
| 4,323,654 A | 4/1982 | Tick |
| 4,420,569 A | 12/1983 | Tick |
| 4,421,947 A | 12/1983 | Kyle |
| 4,424,551 A | 1/1984 | Stevenson |
| 4,940,858 A | 7/1990 | Taylor |
| 4,943,686 A | 7/1990 | Kucharek |

(Continued)

FOREIGN PATENT DOCUMENTS

| DE | 8631853 U1 | 11/1988 |
| EP | 0404435 A1 | 12/1990 |
| EP | 0404435 B1 | 9/1996 |

OTHER PUBLICATIONS

Bayston, R. et al., "Antimicrobial Activity of Silicone Rubber Used in Hydrocephalus Shunts, After Impregnation with Antimicrobial Substances," *J. Clin. Pathol.*, 1981; 34:1057-1062.

(Continued)

*Primary Examiner* — Robert J Hoffberg
*Assistant Examiner* — Hung Dang

(57) ABSTRACT

A system and method for sealing a capacitor bottom in a filtered feedthrough. The feedthrough comprises a ferrule, a capacitor, at least one terminal pin and a support structure. The support structure includes at least one projection that extends into an aperture of the capacitor. The projection includes an opening through which the at least one terminal pin extends such that, in an assembled state, the terminal pin extends through the opening of the projection and the aperture of the capacitor.

24 Claims, 8 Drawing Sheets

(56) References Cited

U.S. PATENT DOCUMENTS

| | | |
|---|---|---|
| 5,015,530 A | 5/1991 | Brow |
| 5,021,307 A | 6/1991 | Brow |
| 5,089,446 A | 2/1992 | Cornelius |
| 5,104,738 A | 4/1992 | Brow |
| 5,104,755 A | 4/1992 | Taylor |
| 5,175,067 A | 12/1992 | Taylor |
| 5,294,241 A | 3/1994 | Taylor |
| 5,306,581 A | 4/1994 | Taylor |
| 5,333,095 A | 7/1994 | Stevenson |
| 5,648,302 A | 7/1997 | Brow |
| 5,650,759 A | 7/1997 | Hittman |
| 5,693,580 A | 12/1997 | Brow |
| 5,817,984 A | 10/1998 | Taylor |
| 5,821,011 A | 10/1998 | Taylor |
| 5,825,608 A | 10/1998 | Duva |
| 5,851,222 A | 12/1998 | Taylor |
| 5,866,851 A | 2/1999 | Taylor |
| 5,867,361 A | 2/1999 | Wolf |
| 5,870,272 A | 2/1999 | Seifried |
| 5,871,513 A | 2/1999 | Taylor |
| 5,902,326 A | 5/1999 | Lessar |
| 6,031,710 A | 2/2000 | Wolf |
| 6,076,017 A | 6/2000 | Taylor |
| 6,090,503 A | 7/2000 | Taylor |
| 6,275,369 B1 | 8/2001 | Stevenson |
| 6,349,025 B1 | 2/2002 | Fraley |
| 6,536,882 B1 | 3/2003 | Hawkins |
| 6,566,978 B2 | 5/2003 | Stevenson |
| 6,603,182 B1 | 8/2003 | Low |
| 6,643,903 B2 | 11/2003 | Stevenson et al. |
| 6,660,116 B2 | 12/2003 | Wolf |
| 6,759,163 B2 | 7/2004 | Frysz |
| 6,759,309 B2 | 7/2004 | Gross |
| 6,768,629 B1 | 7/2004 | Allen |
| 6,855,456 B2 | 2/2005 | Taylor |
| 6,888,233 B2 | 5/2005 | Horning |
| 6,924,165 B2 | 8/2005 | Horning |
| 7,046,499 B1 | 5/2006 | Imani |
| 7,094,967 B2 | 8/2006 | Evans |
| 7,098,117 B2 | 8/2006 | Najafi |
| 7,210,966 B2 | 5/2007 | Taylor |
| 7,214,441 B2 | 5/2007 | Cortright |
| 7,260,434 B1 | 8/2007 | Lim |
| 7,281,305 B1 | 10/2007 | Iyer |
| 7,285,509 B2 | 10/2007 | Bayya |
| 8,373,965 B2 | 2/2013 | Iyer |
| 2001/0050837 A1 | 12/2001 | Stevenson |
| 2003/0083715 A1 | 5/2003 | Taylor |
| 2003/0123215 A1 | 7/2003 | Allen |
| 2003/0125185 A1 | 7/2003 | Hirose |
| 2003/0179536 A1 | 9/2003 | Stevenson |
| 2004/0126953 A1 | 7/2004 | Cheung |
| 2004/0152229 A1 | 8/2004 | Najafi |
| 2004/0180464 A1 | 9/2004 | Horning |
| 2004/0244484 A1 | 12/2004 | Horning |
| 2005/0060003 A1 | 3/2005 | Taylor |
| 2005/0092507 A1 | 5/2005 | Marshall |
| 2005/0186823 A1 | 8/2005 | Ring |
| 2006/0009813 A1 | 1/2006 | Taylor |
| 2006/0173506 A1 | 8/2006 | Rusin |
| 2006/0192272 A1 | 8/2006 | Receveur |
| 2006/0247714 A1 | 11/2006 | Taylor |
| 2006/0290257 A1 | 12/2006 | Heo |
| 2007/0004580 A1 | 1/2007 | Kass |
| 2007/0179554 A1 | 8/2007 | Iyer |
| 2007/0179555 A1 | 8/2007 | Iyer |
| 2007/0217121 A1 | 9/2007 | Fu |
| 2007/0234540 A1 | 10/2007 | Iyer |
| 2007/0239223 A1 | 10/2007 | Engmark |
| 2007/0260282 A1 | 11/2007 | Taylor |
| 2008/0060844 A1 | 3/2008 | Teske |
| 2008/0118831 A1 | 5/2008 | Jouanneau-Si-Larbi |
| 2009/0079517 A1 | 3/2009 | Iyer |
| 2009/0079518 A1 | 3/2009 | Iyer |
| 2009/0079519 A1 | 3/2009 | Iyer |

OTHER PUBLICATIONS

Diemat DM2700PF/DM2760PF, Low-Temperature Sealing Glass Preforms—Product Data Sheet, Jul. 24, 2006, 4 pgs.

Diemat DM2995PF Series Lead (Pb)-Free Sealing Glass Preforms—Preliminary Data Sheet, Aug. 27, 2006, 4 pgs.

Diemat, Inc., Material Safety Data Sheet—DM2995PF, Aug. 23, 2006, 4 pgs.

International Search Report for PCT/US2008/077179 dated May 25, 2009, 4 pgs.

International Search Report for PCT/US2009/050191 dated Oct. 6, 2009, 4 pgs.

Yourassowsky, E. et al., "Combination of Minocycline and Rifampicin Against Methicillin-and Gentamicin-Resistant Staphylococcus aureus," *J. Clin. Pathol.*, 1981; 34:559-563.

(PCT/US2010/023691) PCT Notification of Transmittal of the International Search Report and the Written Opinion of the International Searching Authority, May 4, 2010.

FILTERED FEEDTHROUGH ASSEMBLY AND ASSOCIATED METHOD

This application is a continuation of U.S. patent application Ser. No. 12/368,847, filed Feb. 10, 2009 (pending), which is incorporated herein by reference.

FIELD

The present disclosure relates to electrical feedthroughs for implantable medical devices and, more particularly, a capacitor assembly for a filtered feedthrough.

INTRODUCTION

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Electrical feedthroughs serve the purpose of providing an electrical circuit path extending from the interior of a hermetically sealed container to an external point outside the container. A conductive path is provided through the feedthrough by a conductor pin which is electrically insulated from the container. Many feedthroughs are known in the art that provide the electrical path and seal the electrical container from its ambient environment. Such feedthroughs typically include a ferrule, the conductor pin or lead and a hermetic ceramic seal which supports the pin within the ferrule. Such feedthroughs are typically used in electrical medical devices such as implantable pulse generators (IPGs). It is known that such electrical devices can, under some circumstances, be susceptible to electromagnetic interference (EMI). At certain frequencies for example, EMI can inhibit pacing in an IPG. This problem has been addressed by incorporating a capacitor structure within the feedthrough ferrule, thus shunting any EMI at the entrance to the IPG for high frequencies. This has been accomplished with the aforementioned capacitor device by combining it with the feedthrough and incorporating it directly into the feedthrough ferrule. Typically, the capacitor electrically contacts the pin lead and the ferrule.

Many different insulator structures and related mounting methods are known in the art for use in medical devices wherein the insulator structure also provides a hermetic seal to prevent entry of body fluids into the housing of the medical device. The feedthrough terminal pins, however, are connected to one or more lead wires which effectively act as an antenna and thus tend to collect stray or electromagnetic interference (EMI) signals for transmission to the interior of the medical device. In some prior art devices, ceramic chip capacitors are added to the internal electronics to filter and thus control the effects of such interference signals. This internal, so-called "on-board" filtering technique has potentially serious disadvantages due to intrinsic parasitic resonances of the chip capacitors and EMI radiation entering the interior of the device housing.

In another approach, a filter capacitor is combined directly with a terminal pin assembly to decouple interference signals to the housing of the medical device. In a typical construction, a coaxial feedthrough filter capacitor is connected to a feedthrough assembly to suppress and decouple undesired interference or noise transmission along a terminal pin.

So-called discoidal capacitors having two sets of electrode plates embedded in spaced relation within an insulative substrate or base typically form a ceramic monolith in such capacitors. One set of the electrode plates is electrically connected at an inner diameter surface of the discoidal structure to the conductive terminal pin utilized to pass the desired electrical signal or signals. The other or second set of electrode plates is coupled at an outer diameter surface of the discoidal capacitor to a cylindrical ferrule of conductive material, wherein the ferrule is electrically connected in turn to the conductive housing or case of the electronic instrument.

In operation, the discoidal capacitor permits passage of relatively low frequency electrical signals along the terminal pin, while shunting and shielding undesired interference signals of typically high frequency to the conductive housing. Feedthrough capacitors of this general type are commonly employed in implantable pacemakers, defibrillators and the like, wherein a device housing is constructed from a conductive biocompatible metal such as titanium and is electrically coupled to the feedthrough filter capacitor. The filter capacitor and terminal pin assembly prevent interference signals from entering the interior of the device housing, where such interference signals might otherwise adversely affect a desired function such as pacing or defibrillating.

In the past, feedthrough filter capacitors for heart pacemakers and the like have typically been constructed by preassembly of the discoidal capacitor with a terminal pin subassembly which includes the conductive terminal pin and ferrule. More specifically, the terminal pin subassembly is prefabricated to include one or more conductive terminal pins supported within the conductive ferrule by means of a hermetically sealed insulator ring or bead. See, for example, the terminal pin subassemblies disclosed in U.S. Pat. Nos. 3,920,888; 4,152,540; 4,421,947; and 4,424,551. The terminal pin subassembly thus defines a small annular space or gap disposed radially between the inner terminal pin and the outer ferrule. A small discoidal capacitor of appropriate size and shape is then installed into this annular space or gap, in conductive relation with the terminal pin and ferrule, e.g., by means of soldering or conductive adhesive. The thus-constructed feedthrough capacitor assembly is then mounted within an opening in the pacemaker housing, with the conductive ferrule in electrical and hermetically sealed relation in respect of the housing, shield or container of the medical device.

Although feedthrough filter capacitor assemblies of the type described above have performed in a generally satisfactory manner, the manufacture and installation of such filter capacitor assemblies has been relatively costly and difficult. One common method for forming a feedthrough filter capacitor assembly is to physically couple the capacitor to the insulating structure of the feedthrough by thermal curing of one or more non-conductive epoxy preforms. The installation of such filter capacitor assemblies poses certain problems related to the curing of the epoxy preforms. For example, the epoxy preforms may wick into the annular cavities provided between the capacitor and the terminal pins during curing and thus occupy space that should be filled by a conductive material (e.g., epoxy, solder). This results in a degraded electrical connection between the terminal pins and the capacitors. Additionally, the non-conductive epoxy preforms may seep into the insulating structure and cover cracks that have formed through the braze joint. This may prevent gas from being detected during leak testing and, therefore, may create the impression that a satisfactory hermetic seal has been formed when, in fact, one has not. The use of non-conductive epoxy has been considered mandatory not only because of the physical coupling of the capacitor to the insulating structure, but also because the non-conductive epoxy, when cured, prevents the seeping of conductive material, which is used to electrically couple the capacitor to the pin and ferrule, into the insulating structure of the feedthrough.

The present teachings provide a feedthrough filter capacitor assembly of the type used, for example, in implantable medical devices such as heart pacemakers and the like, wherein the filter capacitor is designed for relatively simplified and economical, yet highly reliable, installation. Further, the present teachings provide a filtered feedthrough assembly utilizing an improved capacitor attachment technique that eliminates the need for non-conductive epoxy and prevents the undesired travel of conductive material, such as epoxy or solder.

SUMMARY

In various exemplary embodiments, the present disclosure relates to a filtered feedthrough assembly comprising a ferrule, a capacitor, at least one terminal pin and a support structure. The capacitor comprises a top portion, a bottom portion, and an inner diameter portion. The inner diameter portion of the capacitor defines at least one aperture extending from the top portion to the bottom portion. The at least one terminal pin extends through the at least one aperture. The support structure is configured to be received within the ferrule, and comprises at least one projection extending from a first side. The at least one projection comprises an inner circumference defining an opening extending through the support structure to a second side opposing the first side. The at least one projection extends into the at least one aperture of the capacitor and the at least one terminal pin extends through the opening.

In various exemplary embodiments, the present disclosure relates to a method of assembling a filtered feedthrough assembly comprising inserting at least one terminal pin, a support structure and a capacitor within a ferrule. The support structure comprises at least one projection extending from a first side, the at least one projection comprising an inner circumference defining an opening extending through the support structure to a second side opposing the first side. The capacitor comprises a top portion, a bottom portion, and an inner diameter portion. The inner diameter portion defines at least one aperture extending from the top portion to the bottom portion. The at least one projection extends into the at least one aperture of the capacitor. The at least one terminal pin extends through the opening and through the at least one aperture.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF DRAWINGS

The present disclosure will become more fully understood from the detailed description and the accompanying drawings, wherein.

DESCRIPTION

Figure 1:
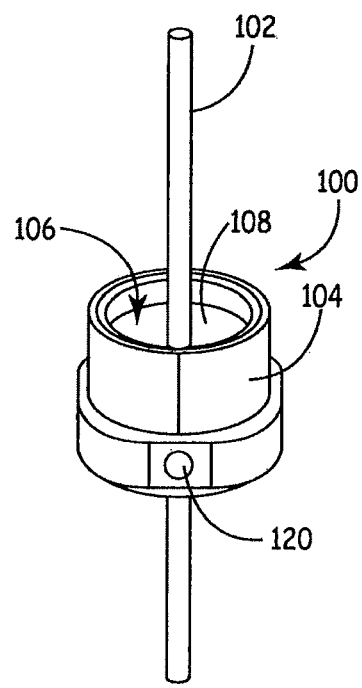
FIGS. 1 and 2 are isometric and cross-sectional views, respectively, of a known unipolar (single pin) feedthrough assembly prior to attachment of a discrete discoidal capacitor.

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

Figure 2:
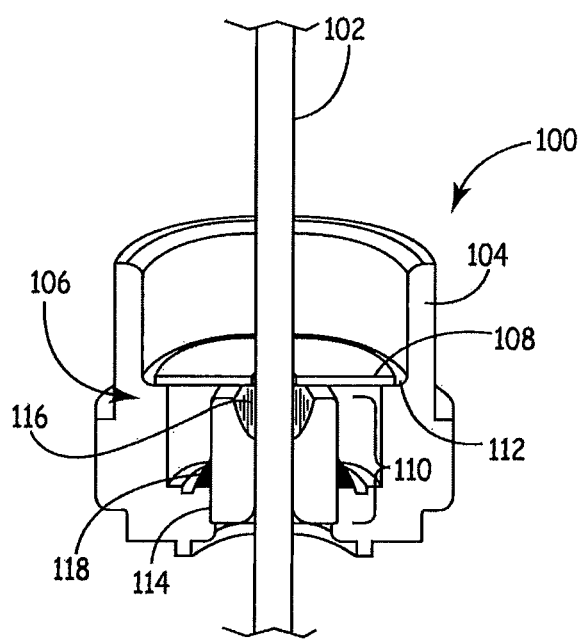

FIGS. 1 and 2 are isometric and cross-sectional views, respectively, of a known unipolar (single pin) feedthrough assembly 100 having a terminal pin 102 extending therethrough. Assembly 100 comprises a generally cylindrical ferrule 104 having a cavity through which pin 102 passes. Ferrule 104 is made of an electrically conductive material (e.g., titanium alloy) and is configured to be fixedly coupled (e.g., welded) to the container of a medical device as described below in conjunction with FIG. 11-12. An insulating structure 106 is disposed within ferrule 104 to secure pin 102 relative to ferrule 104 and to electrically isolate pin 102 from ferrule 104. Insulating structure 106 comprises a supporting structure 108 and a joint-insulator sub-assembly 110, both of which are disposed around terminal pin 102. As will be more fully described below, joint-insulator sub-assembly 110 acts as an insulative seal and may take the form of, for example, a braze joint. Supporting structure 108 is made of a non-conductive material (e.g., polyimide) and rests on an inner ledge 112 provided within ferrule 104. As will be seen in FIG. 3, a discrete discoidal capacitor 150 may be threaded over terminal pin 102 and fixedly coupled to supporting structure 108 to attach the capacitor to feedthrough assembly 100.

As can be seen in FIG. 2, braze joint 110 comprises three main components: an insulator ring 114 (e.g., made from a ceramic material) that insulates pin 102 from ferrule 104, a pin-insulator braze 116 (e.g., made from gold) that couples insulating ring 114 to pin 102, and an insulator-ferrule braze 118 (e.g., made from gold) that couples insulating ring 114 to ferrule 104. Braze joint 110 is exposed along the underside of ferrule 104. When ferrule 104 is fixedly coupled to the container of the medical device, the lower portion of ferrule 104, and thus the lower portion of braze joint 110, may be exposed to body fluids. For this reason, it is important that braze joint 110 forms a hermetic seal between ferrule 104 and terminal pin 102. Braze joint 110 may be leak tested. To permit this test to be performed, an aperture 120 (FIG. 1) is provided through ferrule 104 to the inner annular cavity formed by the outer surface of braze joint 110, the lower surface of supporting structure 108, and the inner surface of ferrule 104. A gas is delivered through aperture 120 into the inner annular cavity, and aperture 120 is plugged. Preferably, a gas of low molecular weight (e.g., helium or hydrogen) is chosen so that it may easily penetrate small cracks in braze joint 110. Feedthrough 100 is then monitored for the presence of the gas proximate braze joint 110 by way of, for example, a mass spectrometer. If no gas is detected, it is concluded that braze joint 110 has formed a satisfactory seal.

Figure 3:
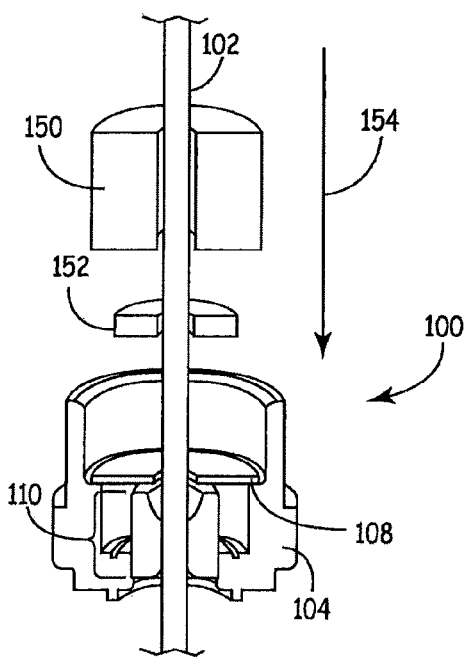
FIGS. 3-5 illustrate a prior art method of attaching a discrete discoidal capacitor to the feedthrough assembly shown in FIGS. 1 and 2.
Figure 4:
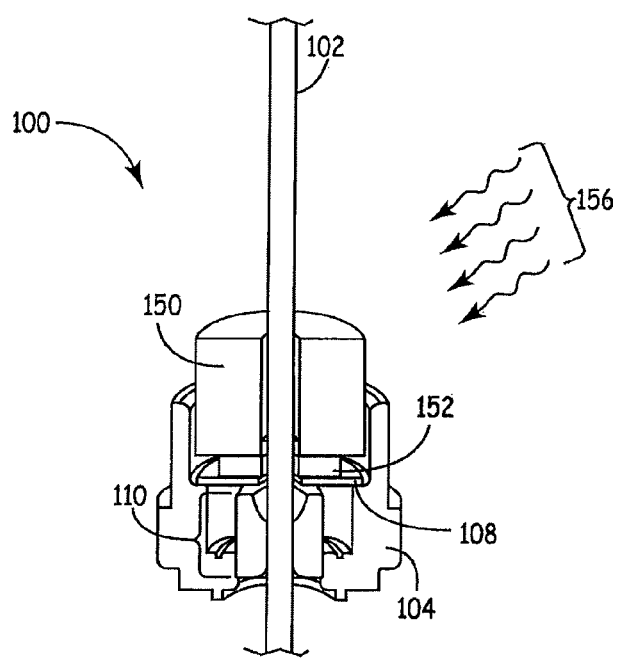
Figure 5:
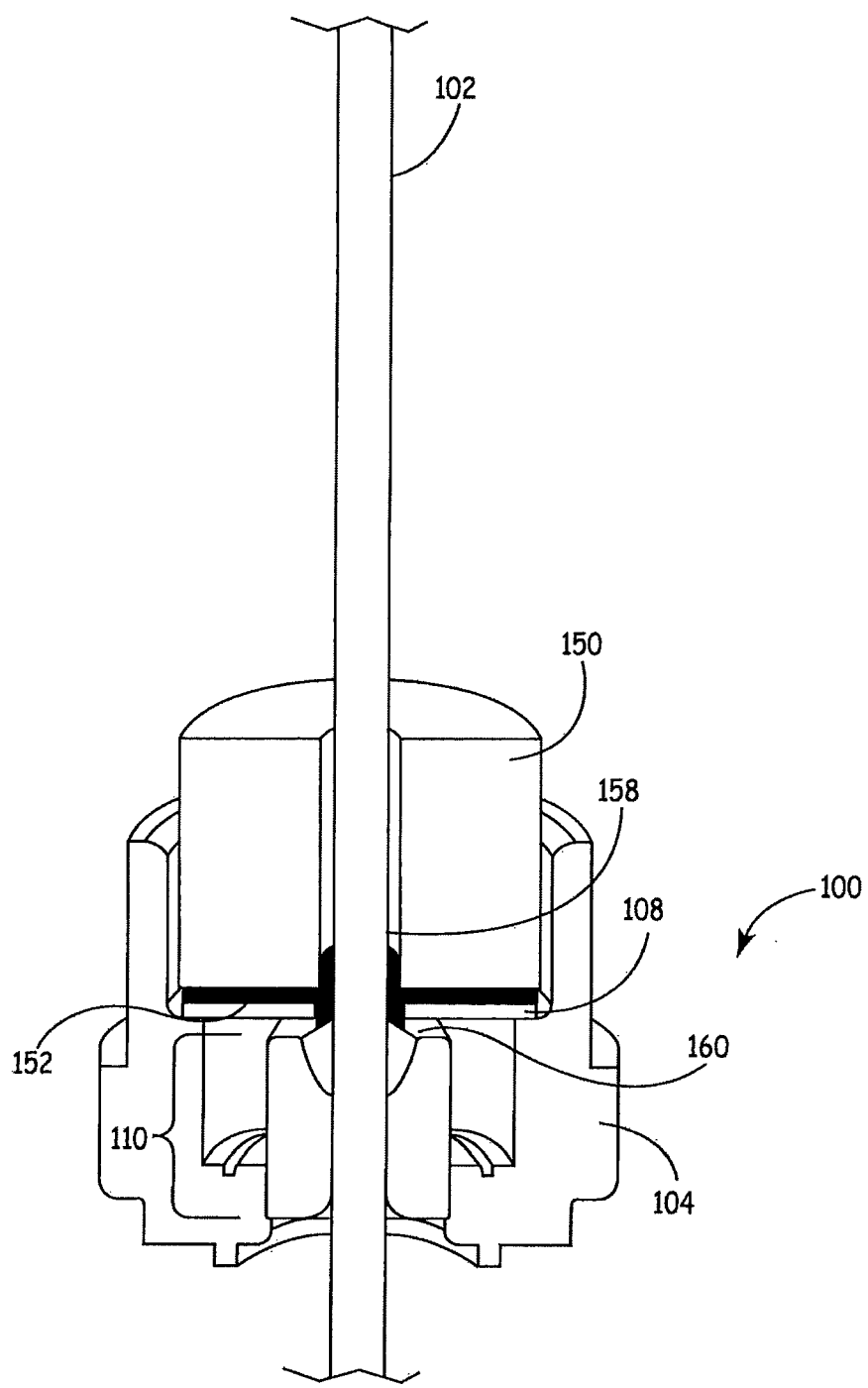

Terminal pin 102 provides a conductive path from the interior of a medical device (not shown) to one or more lead wires exterior to the medical device. As described previously, these lead wires are known to act as antennae that collect stray electromagnetic interference (EMI) signals, which may interfere with the proper operation of the device. To suppress and/or transfer such EMI signals to the container of the medical device, a discrete discoidal capacitor may be attached to feedthrough assembly 100. In particular, the capacitor may be disposed around and electrically coupled to terminal pin 102 and fixedly coupled to supporting structure 108. FIGS. 3-5 illustrate a known manner of attaching a discrete discoidal capacitor 150 to feedthrough assembly 100 shown in FIGS. 1 and 2. The attachment method commences as a ring-shaped preform 152 of non-conductive epoxy is threaded over terminal pin 102 (indicated in FIG. 3 by arrow 154). Capacitor 150 is then threaded over pin 102 and positioned against preform 152 such that preform 152 is sandwiched between capacitor 150 and supporting structure 108. Next, feedthrough assembly 100 is placed within a curing oven and heated to a predetermined temperature (e.g., approximately 175 degrees Celsius) to thermally cure preform 152 (indicated in FIG. 4 by arrows 156) and thus physically couple capacitor 150 to supporting structure 108.

During curing, preform 152 melts and disperses under the weight of capacitor 150, which moves downward toward supporting structure 108. Preform 152 disperses along the annular space provided between the bottom surface of capacitor 150 and the upper surface of supporting structure 108 to physically couple capacitor 150 and supporting structure 108 as described above. In addition, preform 152 may disperse upward into the annular space provided between the inner surface of capacitor 150 and outer surface of terminal pin 102 (shown in FIG. 5 at 158). Dispersal of preform 152 in this manner may interfere with the proper electrical coupling of capacitor 150 to terminal pin 102. Also, during curing, preform 152 may disperse downward into insulating structure 110 (shown in FIG. 5 at 160). This dispersal may result in preform 152 covering any cracks that have formed through braze joint 110 and, consequently, prevent the accurate leak testing of feedthrough assembly 100.

Figure 6:
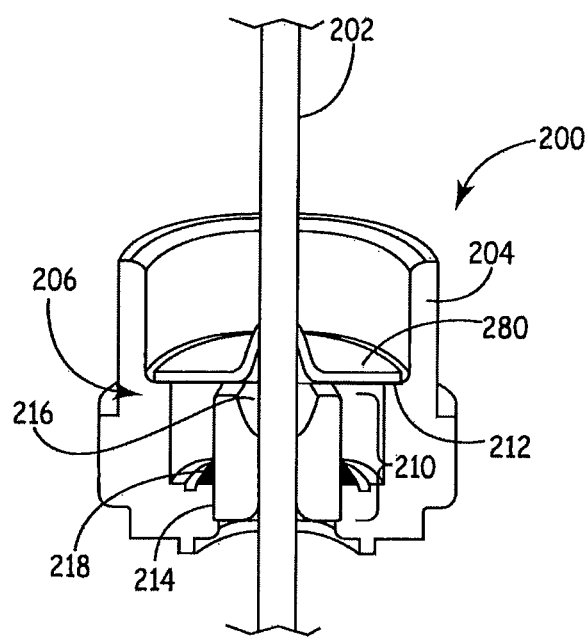
FIG. 6 is a cross-sectional view of a unipolar (single pin) filtered feedthrough assembly according to various exemplary embodiments of the present disclosure prior to attachment of a discrete discoidal capacitor.
Figure 7:
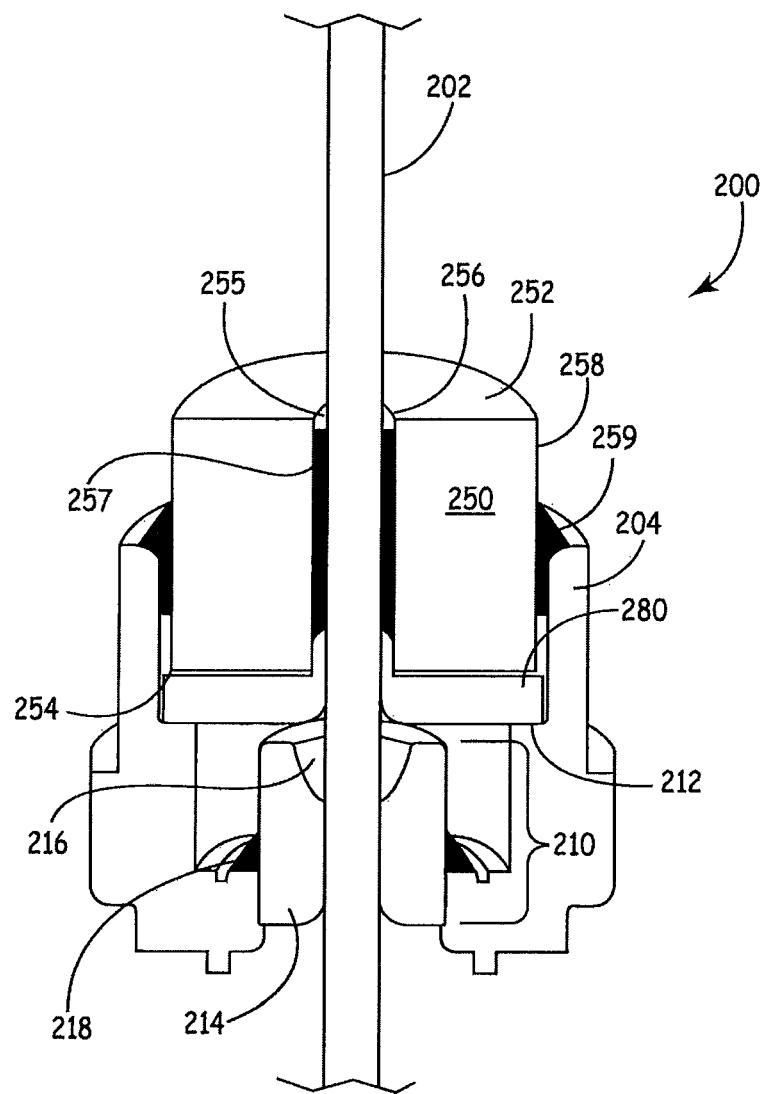
FIG. 7 is a cross-sectional view of a unipolar (single pin) filtered feedthrough assembly with an attached discrete discoidal capacitor according to various exemplary embodiments of the present disclosure.

Referring now to FIGS. 6-7, a filtered feedthrough assembly 200 according to various exemplary embodiments of the present disclosure is illustrated. Filtered feedthrough assembly 200 is unipolar (single pin) and has a terminal pin 202 extending therethrough. Assembly 200 comprises a generally cylindrical ferrule 204 having a cavity through which pin 202 passes. Ferrule 204 is made of an electrically conductive material (e.g., titanium alloy) and is configured to be fixedly coupled (e.g., welded) to the container of a medical device as described below in conjunction with FIGS. 11-12. An insulating structure comprising supporting structure 280 and a joint-insulator sub-assembly 210 is disposed within ferrule 204 to secure pin 202 relative to ferrule 204 and to electrically isolate pin 202 from ferrule 204. Both of the supporting structure 280 and a joint-insulator sub-assembly 210 are disposed around terminal pin 202. The joint-insulator sub-assembly 210 acts as an insulative seal and may take the form of, for example, a braze joint. As described more fully below, supporting structure 280 is made of a non-conductive material (e.g., polyimide, polyetheretherketone (PEEK) or similar material) and rests on an inner ledge 212 provided within ferrule 204. As will be seen, a discrete discoidal capacitor may be threaded over terminal pin 202 and fixedly coupled to supporting structure 280 to attach the capacitor to feedthrough assembly 200.

Braze joint 210 comprises three main components: an insulator ring 214 (e.g., made from a ceramic material) that insulates pin 202 from ferrule 204, a pin-insulator braze 216 (e.g., made from gold) that couples insulating ring 214 to pin 202, and an insulator-ferrule braze 218 (e.g., made from gold) that couples insulating ring 214 to ferrule 204. Braze joint 210 is exposed along the underside of ferrule 204. When ferrule 204 is fixedly coupled to the container of the medical device, the lower portion of ferrule 204, and thus the lower portion of braze joint 210, may be exposed to body fluids. For this reason, it is important that braze joint 210 forms a hermetic seal between ferrule 204 and terminal pin 202, which may be leak tested, as described above.

Terminal pin 202 provides a conductive path from the interior of a medical device (not shown) to one or more lead wires exterior to the medical device. As described previously, these lead wires are known to act as antennae that collect stray electromagnetic interference (EMI) signals, which may interfere with the proper operation of the device. To suppress and/or transfer such EMI signals to the container of the medical device, a discrete discoidal capacitor 250 may be attached to feedthrough assembly 200. In particular, the capacitor 250 may be disposed around and electrically coupled to terminal pin 202 and fixedly coupled to supporting structure 280, described more fully below.

The capacitor 250 includes a top portion 252, a bottom portion 254, an inner diameter portion 256 and an outer diameter portion 258. The inner diameter portion 256 defines an aperture 255, extending from the top portion 252 to the bottom portion 254, through which the terminal pin 202 extends. In the assembled filtered feedthrough assembly 200, the inner diameter portion 256 of capacitor 250 is electrically coupled to the terminal pin 202, e.g., by means of solder or conductive epoxy 257. Similarly, the outer diameter portion 258 of capacitor 250 is electrically coupled to the ferrule 204, e.g., by means of solder or conductive epoxy 259. The inner and outer diameters 256, 258 are each electrically coupled with one of the two sets of electrode plates that are electrically isolated from one another and form the capacitor 250.

Figure 8A:
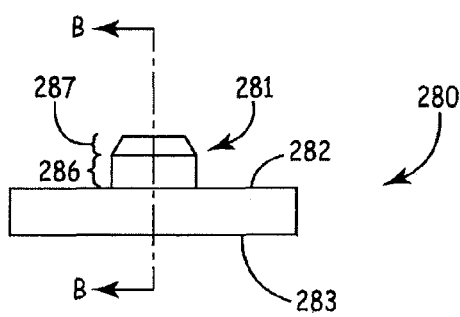
FIG. 8A is a perspective side view of a support structure utilized in a unipolar (single pin) filtered feedthrough assembly according to various embodiments of the present disclosure.
Figure 9A:
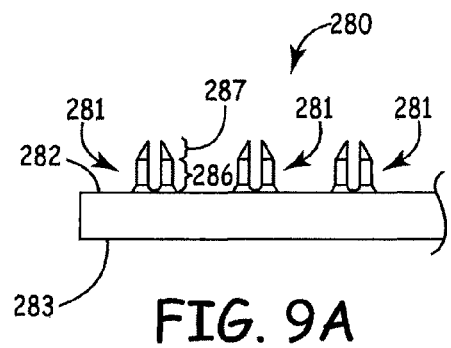
FIG. 9A is a perspective side view of a support structure utilized in a multipolar (multiple pin) filtered feedthrough assembly according to various embodiments of the present disclosure.
Figure 9B:
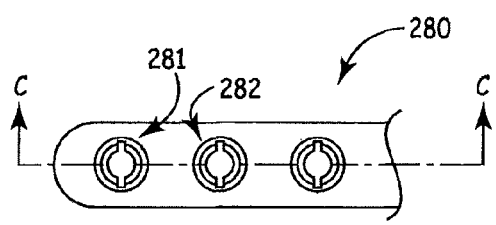
FIG. 9B is a perspective top view of the support structure of FIG. 9A.
Figure 8B:
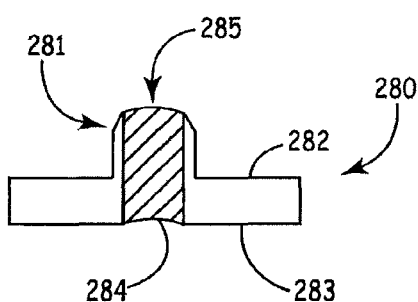
FIG. 8B is a cross-sectional view of the support structure of FIG. 8A taken along line B-B.
Figure 9C:
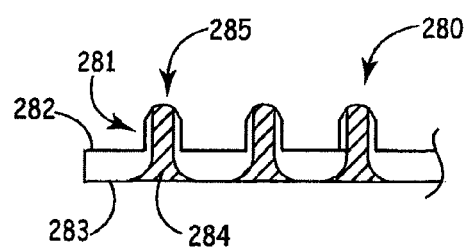
FIG. 9C is a cross-sectional view of the support structure of FIGS. 9A and 9B taken along line C-C.

Referring now to FIGS. 6-9C, a support structure 280 according to various exemplary embodiments of the present disclosure is illustrated. As shown in FIGS. 6-7, support structure 280 is sized and configured to be received within ferrule 204. In the illustrated example, support structure rests upon an inner ledge 212 provided within ferrule 204. As shown in FIGS. 8A-9C, support structure 280 may be designed for use in a unipolar, i.e., single pin, feedthrough assembly as shown in FIGS. 8A-B, or a multipolar, i.e., multiple pin, feedthrough assembly as shown in FIGS. 9A-C. The design differences between a unipolar and multipolar support structure 280 are minor and essentially equate to including the correct number of openings within support structure 280 to accommodate the number of terminal pin(s) 202 in the feedthrough.

The support structure 280 comprises at least one projection 281 extending from a first side 282 of the support structure 280. The inner circumference 284 of the projection 281 defines an opening 285 that extends through the support structure 280 from the first side 282 to a second side 283 opposed thereto. In some exemplary embodiments, the projection 281 includes a cylindrical base portion 286 and a chamfered portion 287. The chamfered portion 287 simplifies insertion of the projection 281 into the aperture 255 of the capacitor 250, as described more fully below.

The opening 285 is sized to receive and mate with terminal pin 202. In some exemplary embodiments, the opening 285 is sized such that the terminal pin 202 is tightly secured in the opening 285, e.g., to create a seal between terminal pin 202 and opening 285. In the exemplary embodiment illustrated in FIGS. 9A-C, the projection 281 is comprised of a bifurcated cylindrical base portion, which is, in its simplest form, a cylindrical projection 281 that is split in two, or more, portions. The split allows for elastic deformation of the projection 281 such that the outer diameter of terminal pin 202 may be greater than the inner circumference 284 of opening 285 in a non-deformed state. Upon insertion of terminal pin 202 into opening 285, the portions of the projection 281 expand outwardly to accommodate the terminal pin 202, while the resiliency of the projection 281 portions provides a force upon terminal pin 202 to assist in the securing and sealing of the terminal pin 202 in opening 285. Additionally, the walls of the opening 285 may be substantially straight, as shown in FIGS. 8A-B, or otherwise contoured, e.g., tapered to provide a conical cross-section as shown in FIGS. 9A-C, to assist in the insertion of terminal pin 202 into the opening 285.

The filtered feedthrough assembly 200 according to various exemplary embodiments may be assembled as follows. The joint-insulator sub-assembly 210 is disposed within ferrule 204 to secure pin 202 relative to ferrule 204 and to electrically isolate pin 202 from ferrule 204, as described more fully above. Support structure 280 may then be inserted within ferrule 204 such that terminal pin 202 extends through opening 285. As described above, the opening 285 of support structure 280 may be sized so as to mate with terminal pin 202 in a secure fashion. A partially assembled filtered feedthrough assembly 200 according to various exemplary embodiments of the present disclosure is illustrated in FIG. 6.

Capacitor 250 is then inserted at least partially within the ferrule 204 such that terminal pin 202 extends through, and the projection 281 is partially received within, aperture 255. In some exemplary embodiments, projection 281 and aperture 255 are sized such that the projection 281 is tightly secured in the aperture 255, e.g., to create a seal between projection 281 and aperture 255. In this manner, support structure 280 may be physically coupled to capacitor 250 without the use of non-conductive epoxy or other compound as in the prior art, which not only simplifies the assembly process, but also prevents the intrusion of the non-conductive epoxy into the joint-insulator sub-assembly 210. Furthermore, projection 281 may be sized and positioned such that the terminal pin 202 is substantially centered within aperture 255, which will assist in the formation of a reliable electrical connection between capacitor 250 and terminal pin 202.

After placement of capacitor 250 within ferrule 204, the inner diameter portion 256 of capacitor 250 is electrically coupled to the terminal pin 202, e.g., by means of solder or conductive epoxy 257. Similarly, the outer diameter portion 258 of capacitor 250 is electrically coupled to the ferrule 204, e.g., by means of solder or conductive epoxy 259. Support structure 280, and specifically the coupling of aperture 255 and projection 281, inhibits or prevents the flow of solder or conductive epoxy 257, 259 into the joint-insulator sub-assembly 210. A fully assembled filtered feedthrough assembly 200 according to various exemplary embodiments of the present disclosure is illustrated in FIG. 7.

Figure 10:
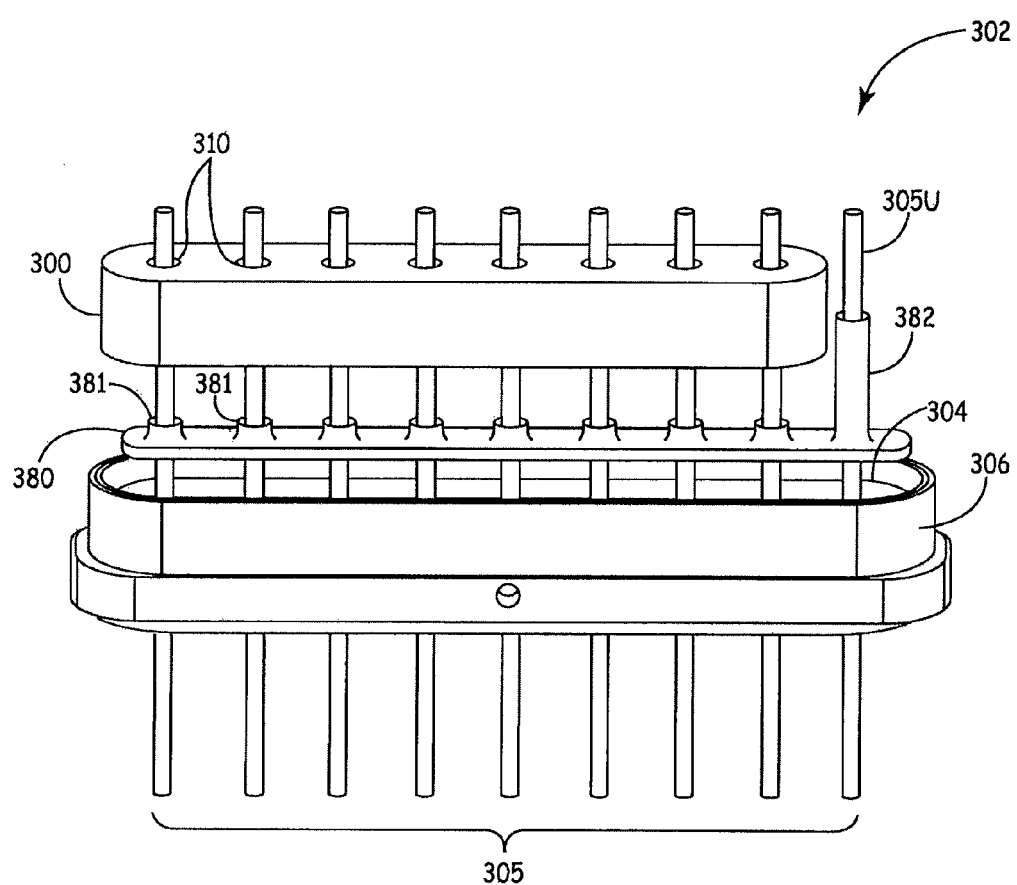
FIG. 10 is an exploded view of a multipolar (multiple pin) filtered feedthrough assembly illustrating the attachment of a monolithic discoidal capacitor in accordance with various exemplary embodiments of the present disclosure.

FIG. 10 illustrates the attachment of a monolithic discoidal capacitor 300 to a multipolar feedthrough assembly 302 in accordance with a various exemplary embodiments of the present invention. Filtered feedthrough assembly 302 comprises a ferrule 306 and an insulating structure 304 disposed within ferrule 306. Filtered feedthrough assembly 302 guides an array of terminal pins 305 through the container of a medical device to which ferrule 304 is coupled (shown in FIG. 12). As described above, terminal pin array 305 and the lead wires to which array 305 is coupled may act as an antenna and collect undesirable EMI signals. Monolithic discoidal capacitor 300 may be attached to feedthrough assembly 302 to provide EMI filtering. Capacitor 300 is provided with a plurality of terminal pin-receiving apertures 310 therethrough. Capacitor 300 is inserted over terminal pin array 305 such that each pin in array 305 is received by a different aperture 310 and placed in an abutting relationship with insulating structure 304. If desired, one terminal pin in array 305 may be left unfiltered as shown in FIG. 10 to serve as an RF antenna. Support structure 380 is provided between insulating structure 304 and capacitor 300. Capacitor 300 may be coupled to support structure 380, such as by projections 381 on support structure 380 being securely received within terminal pin-receiving apertures 310, similarly to that discussed above in regard to a unipolar feedthrough assembly 200. Furthermore, a sleeve 382 may be included on support structure 380 to assist in the isolation of the unfiltered pin 305U from capacitor 300.

Figure 11:
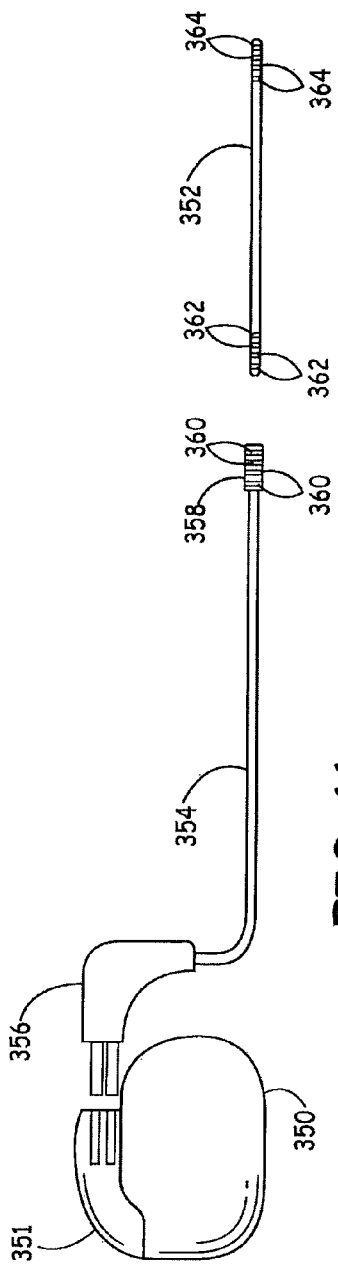
FIG. 11 is a perspective view of a partially disassembled implantable medical device.

FIG. 11 is an exploded view of an implantable medical device (e.g., a pulse generator) 350 coupled to a connector block 351 and a lead 352 by way of an extension 354. The proximal portion of extension 354 comprises a connector 356 configured to be received or plugged into connector block 351, and the distal end of extension 354 likewise comprises a connector 358 including internal electrical contacts 360 configured to receive the proximal end of lead 352 having electrical contacts 362 thereon. The distal end of lead 352 includes distal electrodes 364, which may deliver electrical pulses to target areas in a patient's body (or sense signals generated in the patient's body, e.g., cardiac signals).

Figure 12:
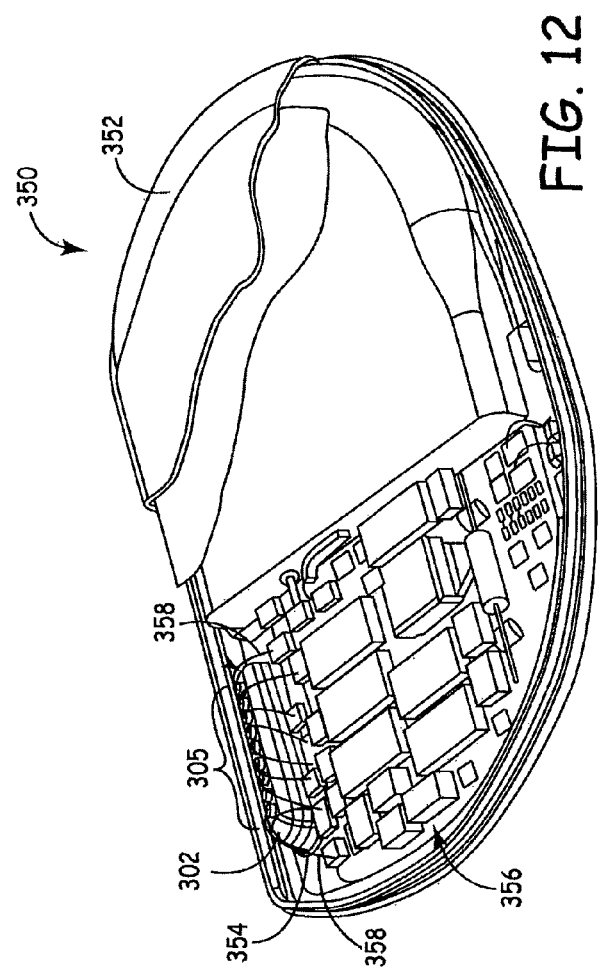
FIG. 12 is an isometric cutaway view of an implantable medical device incorporating the multipolar (multiple pin) filtered feedthrough assembly of FIG. 10.

After a capacitor 300 has been attached to feedthrough assembly 302 in the manner described above, assembly 302 may be welded to the housing of an implantable medical device 350 as shown in FIG. 12. Medical device 350 comprises a container 352 (e.g. titanium or other biocompatible material) having an aperture 354 therein through which feedthrough assembly 302 is disposed. As can be seen, each terminal pin in array 305 has been trimmed and is electrically connected to circuitry 356 of device 350 via a plurality of connective wires 358 (e.g., gold), which may be coupled to terminal pin array 305 by wire bonding, laser ribbon bonding, or the like. After installation, feedthrough assembly 302 and capacitor 300 collectively function to permit the transmission of relatively low frequency electrical signals along the terminal pins in array 305 to circuitry 356 while shunting undesired high frequency EMI signals to container 352 of device 350.

The broad teachings of the disclosure can be implemented in a variety of forms. Therefore, while this disclosure includes particular examples, the true scope of the disclosure should not be so limited since other modifications will become apparent upon a study of the drawings, the specification, and the following claims.

What is claimed is:

1. A filtered feedthrough assembly, comprising:
a ferrule;
a capacitor comprising a top portion and a bottom portion, wherein at least one aperture is defined through the capacitor from the top portion to the bottom portion;
at least one terminal pin extending through the at least one aperture; and
a support structure configured to be received within the ferrule, wherein the support structure comprises:
a first side;
a second side opposing the first side; and
at least one projection extending from the first side prior to insertion of the at least one terminal pin through the support structure, wherein an opening is defined through the at least one projection and extends to the second side of the support structure,
wherein the at least one projection of the support structure extends into the at least one aperture of the capacitor such that a seal is created between the at least one projection and the at least one aperture defined through the capacitor, wherein the seal is created between the at least one projection and the at least one aperture defined through the capacitor when and upon the insertion of the at least on projection of the support structure into the at least one aperture of the capacitor, and further wherein the at least one terminal pin extends through the opening defined through the at least one projection such that the at least one terminal pin is sealed in the opening defined through the at least one projection, wherein another seal is created between the at least one terminal pin and the opening defined through the at least one projection when and upon insertion of the at least one terminal in the opening defined through the at least one projection.

2. The filtered feedthrough assembly of claim 1, wherein the at least one projection comprises a bifurcated cylindrical base portion.

3. The filtered feedthrough assembly of claim 1, wherein the opening tapers from the second side to the first side such that the opening has a conical cross-section.

4. The filtered feedthrough assembly of claim 1, wherein the second side of the support structure rests on an inner ledge of the ferrule.

5. The filtered feedthrough assembly of claim 1, wherein the capacitor further comprises an outer diameter portion and an inner diameter portion defining the at least one aperture of the capacitor, the inner diameter portion being electrically coupled to the at least one terminal pin and the outer diameter portion being electrically coupled to the ferrule.

6. The filtered feedthrough assembly of claim 1, wherein the at least one projection comprises a cylindrical base portion and a chamfered portion.

7. The filtered feedthrough assembly of claim 1, wherein the support structure centers the at least one terminal pin within the at least one aperture.

8. The filtered feedthrough assembly of claim 1, wherein the at least one projection comprises two or more deformable portions.

9. The filtered feedthrough assembly of claim 8, wherein the at least one projection comprises a cylindrical base portion extending from the first side of the support structure, the two or more deformable portions extending from the cylindrical base portion.

10. A filtered feedthrough assembly, comprising:
a ferrule;
a capacitor comprising a top portion and a bottom portion, wherein a plurality of apertures are defined through the capacitor from the top portion to the bottom portion;
at least one terminal pin extending through the at least one aperture; and
a support structure configured to be received within the ferrule, wherein the support structure comprises:
a first side;
a second side opposing the first side; and
a plurality of projections extending from the first side thereof, wherein an opening is defined through each of the projections of the plurality of projections with the opening extending to the second side of the support structure, wherein each of one or more projections of the plurality of projections extends into a corresponding aperture of the capacitor such that a seal is created between the projection and the corresponding aperture, and further wherein each of one or more terminal pins of the plurality of terminal pins extends through a corresponding opening defined through a projection of the plurality of projections such that the terminal pin is secured and sealed in the corresponding opening.

11. The filtered feedthrough assembly of claim 10, wherein the number of apertures defined through the capacitor is less than the number of projections extending from the first side of the support structure such that at least one terminal pin extending through at least one opening defined through at least one projection of the plurality of projections is not coupled to the capacitor.

12. A filtered feedthrough assembly comprising:
a ferrule;
a capacitor comprising a top portion and a bottom portion, wherein at least one aperture is defined through the capacitor from the top portion to the bottom portion;
at least one terminal pin extending through the at least one aperture; and
a support structure configured to be received within the ferrule, wherein the support structure comprises:
a first side;
a second side opposing the first side; and
at least one projection extending from the first side, wherein each projection of the at least one projection comprises two or more deformable portions, wherein an opening is defined through the at least one projection and extends to the second side of the support structure, wherein the at least one projection of the support structure extends into the at least one aperture of the capacitor, and further wherein the at least one terminal pin extends through the opening defined through the at least one projection, wherein a seal is created between the at least one projection and the at least one aperture defined through the capacitor when and upon the insertion of the at least one projection of the support structure into the at least one aperture of the capacitor, and further wherein another seal is created between the at least one terminal pin and the opening defined through the at least one projection when and upon insertion of the at least one terminal in the opening defined through the at least one projection.

13. The filtered feedthrough assembly of claim 12, wherein the at least one projection comprises a cylindrical base portion extending from the first side of the support structure, the two or more deformable portions extending from the cylindrical base portion.

14. The filtered feedthrough assembly of claim 12, wherein each of the two or more deformable portions terminates in a chamfered portion.

15. The filtered feedthrough assembly of claim 12, wherein the at least one projection comprises a bifurcated cylindrical base portion.

16. The filtered feedthrough assembly of claim 12, wherein the second side of the support structure rests on an inner ledge of the ferrule.

17. The filtered feedthrough assembly of claim 12, wherein the capacitor further comprises an outer diameter portion and an inner diameter portion defining the at least one aperture of the capacitor, the inner diameter portion being electrically coupled to the at least one terminal pin and the outer diameter portion being electrically coupled to the ferrule.

18. A filtered feedthrough assembly comprising:
  a ferrule;
  a capacitor comprising a top portion and a bottom portion, wherein a plurality of apertures are defined through the capacitor from the top portion to the bottom portion;
  at least one terminal pin extending through the at least one aperture; and
  a support structure configured to be received within the ferrule, wherein the support structure comprises:
    a first side;
    a second side opposing the first side; and
    a plurality of projections extending from the first side thereof, wherein the at least one projection comprises two or more deformable portions, wherein an opening is defined through each of the projections of the plurality of projections with the opening extending to the second side of the support structure, wherein each of one or more projections of the plurality of projections extends into a corresponding aperture of the capacitor such that a seal is created between the projection and the corresponding aperture, and further wherein each of one or more terminal pins of the plurality of terminal pins extends through a corresponding opening defined through a projection of the plurality of projections such that the terminal pin is secured and sealed in the corresponding opening.

19. The filtered feedthrough assembly of claim 18, wherein the number of apertures defined through the capacitor is less than the number of projections extending from the first side of the support structure such that at least one terminal pin extending through at least one opening defined through at least one projection of the plurality of projections is not coupled to the capacitor.

20. A filtered feedthrough assembly, comprising:
  a ferrule;
  a capacitor comprising a top portion and a bottom portion, wherein at least one aperture is defined through the capacitor from the top portion to the bottom portion;
  at least one terminal pin extending through the at least one aperture; and
  a support structure configured to be received within the ferrule, wherein the support structure comprises:
    a first side;
    a second side opposing the first side; and
    at least one projection extending from the first side prior to insertion of the at least one terminal pin through the support structure, wherein the at least one projection is monolithic with the first side, wherein an opening is defined through the at least one projection and extends to the second side of the support structure, wherein the at least one projection of the support structure extends into the at least one aperture of the capacitor such that a seal is created between the at least one projection and the at least one aperture defined through the capacitor, and further wherein the at least one terminal pin extends through the opening defined through the at least one projection such that the at least one terminal pin is sealed in the opening defined through the at least one projection.

21. The filtered feedthrough assembly of claim 20, wherein a circumferential edge extends between the first side and second side, and further wherein an area defined by a cross-sectional circumference of the at least one projection is less than an area defined by the circumferential edge.

22. A filtered feedthrough assembly, comprising:
  a ferrule;
  a capacitor comprising a top portion and a bottom portion, wherein at least one aperture is defined through the capacitor from the top portion to the bottom portion;
  at least one terminal pin extending through the at least one aperture; and
  a support structure configured to be received within the ferrule, wherein the support structure comprises:
    a first side;
    a second side opposing the first side; and
    at least one projection extending from a the first side prior to insertion of the at least one terminal pin through the support structure, wherein an opening is defined through the at least one projection and extends to the second side of the support structure, wherein the second side having the opening defined therein lies substantially along a plane, wherein the at least one projection of the support structure extends into the at least one aperture of the capacitor such that a seal is created between the at least one projection and the at least one aperture defined through the capacitor, and further wherein the at least one terminal pin extends through the opening defined through the at least one projection such that the at least one terminal pin is sealed in the opening defined through the at least one projection.

23. The filtered feedthrough assembly of claim 22, wherein the support structure lacks any portion thereof that extends beyond the plane along which the second side lies in a direction opposite of the at least one projection extending from the first side.

24. A filtered feedthrough assembly, comprising:
  a ferrule;
  a capacitor comprising a top portion and a bottom portion, wherein at least one aperture is defined through the capacitor from the top portion to the bottom portion;
  at least one terminal pin extending through the at least one aperture; and
  a support structure configured to be received within the ferrule, wherein the support structure comprises:
    a first side;
    a second side opposing the first side; and
    at least one projection extending from the first side prior to insertion of the at least one terminal pin through the support structure, wherein an opening is defined through the at least one projection and extends to the second side of the support structure, wherein the at least one projection of the support structure extends into the at least one aperture of the capacitor such that a seal is created between the at least one projection and the at least one aperture defined through the capacitor, wherein the at least one terminal pin extends through the opening defined through the at least one projection such that the at least one terminal pin is sealed in the opening defined through the at least one projection, wherein the support structure comprises only the at least one projection, and further wherein any and all projections of the at least one projection extend in only a first direction relative to the first side of the support structure.

* * * * *